(12) United States Patent  
Ronchi (10) Patent No.: US 10,067,076 B2  
(45) Date of Patent: Sep. 4, 2018

(54) SCANNING METHOD

(71) Applicant: JOHNSON MATTHEY PUBLIC LIMITED COMPANY, London (GB)

(72) Inventor: Emanuele Ronchi, Cleveland (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/101,953

(22) PCT Filed: Dec. 18, 2014

(86) PCT No.: PCT/GB2014/053767  
§ 371 (c)(1),  
(2) Date: Jun. 6, 2016

(87) PCT Pub. No.: WO2015/097451  
PCT Pub. Date: Jul. 2, 2015

(65) Prior Publication Data  
US 2016/0313261 A1  Oct. 27, 2016

(30) Foreign Application Priority Data

Dec. 23, 2013  (GB) .................................. 1322946.3  
Jan. 3, 2014  (GB) .................................. 1400103.6

(51) Int. Cl.  
*G12B 13/00* (2006.01)  
*G01N 23/02* (2006.01)  
*G01N 23/046* (2018.01)

(52) U.S. Cl.  
CPC .......... *G01N 23/02* (2013.01); *G01N 23/046* (2013.01); *G01N 2223/1013* (2013.01);  
(Continued)

(58) Field of Classification Search  
CPC .......... G01N 23/046; G01N 2223/419; G01N 23/18; G01N 2223/628; G01N 23/06;  
(Continued)

(56) References Cited

U.S. PATENT DOCUMENTS 4,178,510 A   12/1979  Wagner  
4,338,521 A    7/1982  Shaw et al.  
(Continued)

FOREIGN PATENT DOCUMENTS

EP  0 404 118 A2  12/1990  
GB  1 493 593 A  11/1977  
(Continued)

OTHER PUBLICATIONS

Hsieh J Ed—Jiang Hsieh: "Chapter 3. Image Reconstruction", 2009, Computed Tomography: Principles, Design, Artifacts, and Recent Advances, Hoboken, NJ : Wiley Interscience, p. 55-117, ISBN: 978-0-8194-7533-6, XP009161838.

(Continued)

*Primary Examiner* — Taeho Jo  
(74) *Attorney, Agent, or Firm* — Baker & Hostetler LLP (57) ABSTRACT

A scanning method, which is a method of identifying a change in the density of an object, includes arranging a source of ionizing radiation and an array of radiation detectors Dn, where n is an integer from 1 to N, capable of detecting the radiation in such a way that radiation counts are counted by the detectors as the source and detectors are rotated around the object. Detectors are arranged in conjugate pairs so that missing data due to a malfunctioning detector may be filled in from its conjugate.

14 Claims, 3 Drawing Sheets

(52) U.S. Cl.
CPC . *G01N 2223/302* (2013.01); *G01N 2223/419* (2013.01); *G01N 2223/5015* (2013.01)

(58) Field of Classification Search
CPC ..... G01N 2223/302; G01N 2223/5015; G01N 2223/1013
USPC .................................................... 250/252.1
See application file for complete search history.

(56) References Cited

U.S. PATENT DOCUMENTS

| | | | |
|---|---|---|---|
| 4,712,178 A | 12/1987 | Tuy et al. | |
| 5,533,081 A | 7/1996 | Hsieh | |
| 2003/0031295 A1* | 2/2003 | Harding | G01N 23/201 378/86 |
| 2004/0222380 A1* | 11/2004 | Fuchs | A61B 6/032 250/369 |
| 2005/0047553 A1* | 3/2005 | Sembritzki | A61B 6/032 378/207 |
| 2005/0063513 A1 | 3/2005 | Hsieh et al. | |
| 2006/0050838 A1 | 3/2006 | Hagiwara et al. | |
| 2006/0067471 A1* | 3/2006 | Hopkins | G01T 1/2018 378/98.8 |
| 2006/0097179 A1 | 5/2006 | Petrillo et al. | |
| 2007/0034805 A1* | 2/2007 | Hopkins | G01T 1/2018 250/368 |
| 2008/0267345 A1* | 10/2008 | Nagumo | G01B 15/025 378/11 |
| 2009/0245459 A1* | 10/2009 | Goto | A61B 6/032 378/16 |
| 2010/0193697 A1* | 8/2010 | Bal | G01T 1/249 250/370.09 |
| 2011/0168900 A1* | 7/2011 | Dobbs | G01B 15/02 250/360.1 |
| 2012/0085142 A1* | 4/2012 | Rauer | G01F 23/288 73/1.01 |
| 2012/0140876 A1* | 6/2012 | Jung | G01N 23/046 378/20 |
| 2012/0288056 A1* | 11/2012 | Murakoshi | A61B 6/4233 378/37 |
| 2013/0208850 A1* | 8/2013 | Schmitt | G01N 23/20 378/4 |
| 2013/0301798 A1* | 11/2013 | Kang | G01N 23/04 378/53 |
| 2015/0241572 A1* | 8/2015 | Bowdon | G01N 23/046 378/64 |

FOREIGN PATENT DOCUMENTS

| | | |
|---|---|---|
| GB | 1 584 954 A | 2/1981 |
| GB | 1 587 075 A | 3/1981 |
| WO | 03/024332 A2 | 3/2003 |
| WO | 2013/064838 A1 | 5/2013 |

OTHER PUBLICATIONS

Richard A. Ketcham: "New algorithms for ring articfact removal", Developments in X-Ray Tomography V, Proc. of SPIE, vol. 6318, 2006, pp. 1-7, XP040229037.
International Search Report, dated Mar. 30, 2015, from corresponding PCT application.
GB Search Report, dated Jun. 27, 2014, from corresponding GB application.
GB Search Report, dated Mar. 28, 2015, from corresponding GB application.

* cited by examiner

SCANNING METHOD

The present invention relates to a method of scanning a structure to detect changes in density by means of detecting radiation emitted by a radiation source by a radiation detector.

Methods of imaging objects and animals by X-ray tomography and positron-emission tomography are well-known, particularly in the field of medical imaging for diagnostic purposes. U.S. Pat. No. 4,338,521 describes an X-ray scanner for use in computerised tomography which has a detector comprising an array of detector modules, comprising a plurality of photodiodes and a plurality of scintillator crystals and a radiation beam collimator to direct collimated radiation to the scintillator crystals. A fan-shaped beam of x-rays from an x-ray source is directed through a patient to be detected by the detector. The source and detector are rotated around the patient to provide the data from which a tomographic image may be constructed. In positron-emission tomography (PET) a positron emitted by the decay of a radionuclide annihilates on contact with a suitable electron, causing the emission of two gamma photons of 511 keV in opposite directions. The detection of the direction of the gamma photons enables the estimation of the location of the annihilation event and thus the radionuclide within the patient. The PET scanner therefore incorporates an array of detectors which can detect gamma photons placed around the body of a patient. An image of the relative concentration of the radionuclide in the body may be constructed from the number of photons detected at each detector.

Whilst these scanning methods are well-developed and have become common for medical scanning, scanning a dense structure such as a pipeline presents difficulties because the density of the pipeline material is such that radiographic scanning must be done using gamma radiation which is of sufficient energy to penetrate and pass through the structure so that at least some radiation can be detected after the beam has passed through the structure. Gamma scanning of structures such as distillation columns is a standard industrial diagnostic method for measuring changes in density at different parts of the structure, for example to determine the location and integrity of column trays or other internal structures within the column. Normally this type of scanning is carried out with a single gamma source placed adjacent the column to emit a beam of radiation through the column and a radiation detector placed on an opposed part of the column to intersect and measure the radiation that has traversed the column between the source and detector. The source and detector are normally moved so that different parts of the column can be scanned. The use of many different positions and more than one source or detector can provide sufficient data for generating density maps, or tomographs, of the structure which is scanned, although the resolution is generally quite coarse. In order to generate higher resolution density maps, information from a much larger number of radiation paths through the structure must be used than is currently achieved with conventional column scanning methods.

The inspection of pipelines to find flaws such as wall loss, cracks or corrosion pitting is an application in which it would be desirable to use radiation scanning. A known problem for the oil and gas production industry is the inspection of pipelines located underwater, in particular on the sea-bed. Inspection of the interior of the pipeline by the use of pigs is not always possible, for example when the pipeline has varying diameter. Inspection from outside the pipe may be carried out by ultrasonic methods, although this is not suitable for pipelines having an insulation or coating. Gamma scanning can produce useful information about the density through a cross-section of the pipe. In order to produce information about the thickness of the walls of the pipe at sufficiently high resolution to identify small flaws that may be present in the walls of the pipe a large number of radiation paths through the pipe need to be scanned.

A method of scanning pipelines, is described in WO2013/064838. In that method a source of gamma radiation and an array of radiation detectors is rotated around a part to be scanned, such as a pipeline. The detector array is precisely arranged relative to the source so that the scanning can be carried out at high resolution.

A particular application of the method of WO2013/064838 is the scanning of subsea pipelines. In such conditions the scanning apparatus is located remotely from the operators so that the opportunities for servicing the instrument are limited. Therefore it would be an advantage to provide a scanning method which can take account of occasional failures in the instrument.

According to the invention, we provide a scanning method which is a method of identifying a change in the density of an object, said change representing a difference between the density of said object at a first location and the density of said object at a second location adjacent said first location, the method comprising the steps of:

a. arranging a source of ionizing radiation and a linear array of radiation detectors, where n is an integer from 1 to N, capable of detecting said radiation in such a way that
   i. radiation is emitted from the source in the direction of the array of radiation detectors,
   ii. radiation is emitted from the source towards any one of said radiation detectors along a radiation path, said radiation path being defined at each end by the source and the area of each detector facing said source;
   iii. up to N of said radiation paths may pass through said object; and
   iv. said source and said detector array are located in fixed positions relative to one another and movable along an arcuate scanning path around said object;
   wherein said detector array comprises a plurality of N radiation detectors D which are arranged symmetrically opposite said source in such a way that conjugate pairs of detectors are arranged at equal angles from the source;
b. positioning the source and detector array at a known position on said scanning path;
c. moving said source and detector array along said scanning path so that the source and detector array rotate through 360 degrees around said object;
d. acquiring count data from each detector at a plurality of positions on said scanning path, said count data being related to the number of photons of radiation emitted by the source which have been detected by said detector during the count period;
e. converting count data acquired by each detector at each position by means of a fan to parallel beam conversion algorithm to converted count data;
f. selecting count data from at least one detector of each said conjugate pair;
g. deriving information concerning the density of the object at different positions in the plane of the scanning path from said count data.

A scanning apparatus according to the invention comprises: a source of ionizing radiation and an array of radiation detectors, capable of detecting said radiation, said source and detector array being arranged in such a way that i. radiation is emitted from the source in the direction of the array of radiation detectors,
ii. radiation is emitted from the source towards any one of said radiation detectors along a radiation path, said radiation path being defined at each end by the source and the area of each detector facing said source;
iii. up to N of said radiation paths may pass through an object which is to be scanned; and
iv. said source and said detector array are located in fixed positions relative to one another and movable along an arcuate scanning path around said object;
wherein said detector array comprises a plurality of N radiation detectors D which are symmetrically arranged opposite said source in such a way that conjugate pairs of detectors are arranged at equal angles from the source;

means to move said source and detector array along said scanning path so that the source and detector array rotate through 360 degrees around said object; data processing means which is programmed to a. acquire count data from each detector, at a plurality of positions on said scanning path, said count data being related to the number of photons of radiation emitted by the source which have been detected by said detector during the count period;
b. convert count data acquired by each detector at each position by means of a fan to parallel beam conversion algorithm to converted count data;
c. select count data from at least one detector of each said conjugate pair; and
d. derive information concerning the density of the object at different positions in the plane of the scanning path from said count data.

As the skilled person knows, the amount of electromagnetic radiation which passes from the source of radiation to a detector is directly related to the density and thickness of the material through which the radiation passes. When the thickness of material is constant, a more dense material attenuates the radiation more than a less dense material. Therefore the amount of radiation (indicated by the count of photons detected by the detector) reaching the detector is higher for less dense materials than for more dense materials.

Count data may represent a number of counts detected by the detector within a defined period of time, for example the count period. Count data may be expressed as count rates, i.e. the number of counts per period of time, e.g. counts per second.

Count data may be selected from at least from at least one detector of each said conjugate pair on the basis of the count data counted by each said detector. The method may include the step of comparing the count data acquired by each detector of a conjugate pair to determine whether either of said detectors is defective. If a defective detector is found then count data from the other detector in its conjugate pair may be selected. A defective detector may be recognised if its count data is consistently abnormally low or zero. To determine whether its data is abnormally low or abnormally high, its data may be compared with its paired detector or with a predetermined range of value of counts which would be expected from the detector.

The method may include a step of calibrating the detectors. This step may be carried out in the absence of the object to be scanned. This step may be carried out before the scan is performed. Preferably the calibration step is carried out in the same or substantially the same environmental conditions as will be used for the scan. For example, when the method is used to scan a subsea pipeline, the calibration may be carried out near the pipeline so that seawater of similar pressure, temperature and salinity is present between the source and detector as will be present during the scan. The calibration step may include obtaining an energy spectrum scan for each detector in the array. The information from the energy spectrum scan may be used to identify suitable energy windows within which to count photons detected by the detector. A broken or defective detector may also be identified from its energy spectrum. When such a broken detector has been identified in a calibration step, data from its paired conjugate detector may be selected in step (f). The information from the energy spectrum scan may be used to identify which detector of a conjugate pair of detectors offers the highest resolution. Such information may be obtained from the shape of the energy spectrum. Count data from the detector offering the highest resolution may be selected in step (f).

The step of deriving information concerning the density of the object at different positions in the plane of the scanning path from said count data may include calculating normalised count data from the count data recorded by a detector at each position. In this way, variations in the counts acquired by each of the detectors may be clearly identified. Normalised count data values may be calculated by dividing the count data by a mean value of the count data form a particular detector at all positions. The mean value may be the arithmetic mean, i.e. the sum of all counts recorded by detector n at all positions divided by the number of angular positions at which count data has been collected. Alternatively a different mean value may be used for normalisation, for example mean of squares, sum of squares or log mean.

In addition to, or instead of, normalising the count data values for each detector, values may be normalised for each of the plurality of angular positions over all detectors. That means, for example, calculating the mean count value detected by all detectors at a particular angular position and then dividing all count data values for that position by the calculated mean.

Normalisation of the count data may be carried out by any other data normalisation method, The normalised count data may be collated in a matrix with rows and columns corresponding to individual detectors and angular positions. The matrix may be displayed to an operator. By displaying the normalised count data in the form of a matrix, it is possible to observe patterns within the data from which discontinuities in the density of the object at a particular location may be inferred. When the matrix is displayed, it may be advantageous to represent the normalised count data in the matrix in the form of symbols. A symbol may be used to represent a selected range of normalised count data. Different symbols may represent different ranges of values within the normalised count data. Count data higher than the mean, indicating a material less dense than the mean density, may be represented by one or more different symbols. Count data less than the mean for any detector, indicating a material more dense than the mean density, may be represented by one or more different symbols. The symbols may take the form of coloured dots, pixels or blocks where each colour represents a selected range of normalised count data.

The matrix of count data may be analysed by pattern recognition algorithms using data processing software. In such a case, the location and characteristics of any discontinuities detected by analysis of any patterns found within the matrix of count data may be displayed to an operator.

Patterns within a normalised count data matrix indicate a change in the density of the object. This may indicate a defect within the object. For example when a pattern of normalised counts greater than the mean is found, indicating a less dense portion of the object, such a pattern may be caused by a loss of material through damage caused by corrosion, impact or other failure. When the object which is scanned is a pipeline for example, detection of such a discontinuity may enable the cause to be remedied before a failure of the pipeline occurs which can lead to leakage of contents from the pipeline. As another example, a pattern of normalised counts less than the mean indicates a more dense portion of the object. Such a pattern may be caused, for example, by a dense solid or semi-solid material filling a portion of a pipeline, which may reduce capacity for fluid flow through the pipeline.

A tomographic image may be constructed from the count data obtained from the detectors. A tomographic image is a representation of the shape and material characteristics (which may include the density) of the object. A tomographic image is convenient for the user to interpret because it is possible to indicate on the representation the size and location of any feature found in the tomography scan. Methods for constructing a tomographic image from a plurality of radiation count measurements are known to the person skilled in the art of radiation tomography and are not within the scope of this patent specification.

The count period may be varied according to the requirements of the method. The count period should be selected to allow a number of counts to be detected within the count period which is statistically distinguishable from "noise". The random error in the number of counts reduces as the number of counts increases. However, where the object is made from thick and/or dense materials, such as a pressure-resistant steel pipeline for example, the radiation from the source is highly attenuated by the object so that a relatively small number of photons penetrates the object to be detected by a detector. In such a case, in order to increase the number of photons detected, either the number or energy of photons emitted by the source must be increased (i.e. a larger or more energetic source is required) or the count period must be increased. The size or energy of the source may be constrained by safety considerations. The count period should not be so long as to make scanning of the object impractical. The count period may be less than a second. In an example, the count period may be selected to be within the range from 0.1 to 30 seconds.

The scanning path is arcuate. The scanning path may lie within a plane parallel to the plane of the detector array. Normally the part of the object to be scanned lies wholly within the scanning path. The source and detector array therefore move along the scanning path so as to rotate around the object. Positions x lie on the scanning path and are angularly offset from one another. The positions for which count data is acquired may be equally angularly spaced or the angular spacing between positions may be different. The number of positions at which count data is acquired affects the resolution of the scanning method and the precision at which a change in density may be located. In one embodiment, the number of positions (X) may be 360 where each position is spaced at one degree of angle from adjacent positions on the scanning path and the scanning path is circular. For a circular scanning path it is preferred that X lies between 100 and 2000. For a circular scanning path it is preferred that X lies between 180 and 1450.

The method may be carried out by acquiring data from the detectors as the source and detector move along the scanning path. Data may be acquired from the detectors continually and recorded together with a record of the position at which the data was acquired. The positions of data collection may then be banded into a series of angular intervals related to the start position p0. Such angular intervals may be regular angular intervals. The angular intervals may be selected to be separated by at least a degree or less than a degree. For example, a continuous acquisition of data may be banded into angular intervals of half or one degree or a quarter of one degree. When the source and detector array are moved through a complete circle and the count data is banded into intervals of one quarter of a degree, X is 1440. The speed of movement of source and detector and the angular interval between positions x affects the count period. In a working embodiment of the invention for scanning steel pipeline we have found that a circular scanning path may be completed in 60 minutes or less. When the count data is banded into angular intervals of one quarter degree, the effective count period is 2.5 seconds. The speed of movement along the scanning path may be constant.

The number of detectors N may be greater than 20 and may be greater than 50. The number of detectors which acquire count data may affect the resolution of the scanning method, the time taken to complete a scan and the precision at which a change in density may be located.

The count data may be adjusted according to a calibration. In one embodiment of the method a calibration may be carried out by acquiring count data at each position x in the presence of a known object of consistent density. The known "object" may comprise air or water which fills the space between the source and detector. Calibration count data may be stored in a data processor memory. The calibration adjustment may be made by subtracting or dividing the calibration count data (or a derivative of the count data) from the count data acquired during the scanning method.

The counts data are converted to converted counts data by means of a fan to parallel beam conversion algorithm. The use of fan to parallel beam conversion is known in the field of radiation tomography where measurements are carried out using a radiation beam which is fan-shaped, originating from a small or point source. Suitable fan to parallel beam conversion algorithms are available to the skilled person. The conversion facilitates interpretation of the count data as an attenuation profile of the object along a plane passing through the centre of the instrument. This may allow more intuitive and straightforward interpretation of results.

The scanning apparatus may comprise a pipe-scanning apparatus of the type described in WO2013/064838. Alternatively the scanning apparatus may comprise a different apparatus in which radiation is used to estimate the density along a path through an object or structure.

In a typical scanning apparatus, the source may be housed in a source unit comprising a source of penetrating radiation, a source-holder and a collimator. The collimator and source-holder may be combined. The collimator is formed of a material which is highly attenuating to the radiation emitted by the source and is normally formed of a heavy alloy material of the type known and commonly used for shielding radiation of the appropriate energy and type. The collimator is located and adapted to limit the radiation emitted by the source unit to a predetermined beam shape and direction. Preferably the radiation beam is shaped by the collimator to form a fan, cone, frusto-cone, or sector in each case having the source as origin. A preferred beam shape is a cylindrical sector, i.e. a sector having a thickness rather than being planar. Preferably the beam is collimated to provide a beam area at the location of the detector(s) which has the same general shape and area as the combined detecting surface(s) of the array of detectors. The source unit may be mounted on a support.

The radiation source is selected by the transparency to the radiation of the material(s) to be measured, e.g. a vessel and/or its contents (i.e. the attenuation coefficient of the medium) and the availability of suitable sources and detectors. For scanning large solid structures such as process vessels and pipelines, suitable sources of gamma include $^{60}$Co and $^{137}$Cs, $^{133}$Ba, $^{241}$Am, $^{24}$Na and $^{182}$Ta, however any gamma-emitting isotope of sufficient penetrating power could be used, and many such are already routinely used in density gauges, such as those used as level measurement devices. Usually, the half-life of the radioisotope used will be at least 2, and desirably at least 10, years. The half-lives of the radioisotopes mentioned above are: $^{137}$Cs gamma about 30 years, $^{133}$Ba about 10 years and $^{241}$Am about 430 years. Suitable sources generally emit radiation at energies between about 40 and 1500 keV.

The source unit may include one or more than one source. The scanning method may utilise more than one source unit if required.

The scanning apparatus may comprise an array of radiation detectors. For example the scanning unit may comprise an array of at least 10 detectors. The detector, or each of the detectors, may comprise a scintillator, normally supported in a suitable position so that a surface thereof, which may be referred to as the detecting surface, intersects a path of radiation emitted by the source at a particular distance from and a particular angle to the radiation source. The detector or each detector of a detector array may be housed within a collimator which reduces the detection of radiation impinging on the detector from an angle outside the angle of a linear radiation path from the source. The collimator comprises a material which is impermeable to the radiation emitted by the source. The collimator may cover a part of the detecting surface of the detector to delimit the portion of the detecting surface on which radiation may impinge.

When the detector unit comprises more than one detector, deployed in the form of an array of detectors, a preferred embodiment of the invention comprises a block of shielding material (a "detector block") having openings extending inwardly from a surface of the block, each opening containing a detector, the detecting surface being accessible to radiation from outside the block. A portion of the detecting surface may be covered by shielding material for the purposes of delimiting the area of the detecting surface or for mechanically retaining the detector within the opening. The non-detecting surfaces of the detector may optionally be enclosed partially or wholly within the opening and covered by the shielding material. The detector block includes means by which the collecting surface of the scintillator(s) may be brought into contact with a photodetector or a light transmitter. Such means may take the form of an open passage through which the scintillator extends so that the collecting surface is accessible to the photodetector or light transmitter.

When the detector comprises a scintillation material, such as a scintillation crystal or a polymeric scintillator, a photodetector is provided which is optically coupled to the scintillator in order to detect and measure light generated by the scintillator in response to photons of radiation from the source. The photodetector may be a photodiode, photomultiplier tube (PMT), a silicon photomultiplier or other suitable light detecting device. The photodetector generates an electrical signal in response to light entering it through an optical window. The wavelengths detected by the photodetector should be matched as far as possible to the wavelengths generated by the scintillator to maximise the detection efficiency. Normally a photodetector is provided for each scintillator so that the amount of radiation detected by each scintillator can be measured independently of the other scintillators.

Each detecting surface preferably forms a tangent to an arc of a circle having a radiation source as its origin. In one embodiment, each detector surface forms a tangent to the surface of a part of a sphere having the radiation source as its origin.

Other forms of radiation detector may be employed in a scanning apparatus of the invention. For example, Geiger-Müller tubes or other detectors may be used.

The apparatus further comprises a signal/data processor for operating on the electrical signal from the detectors in the detector unit(s) and a controller to control the operation of the apparatus. Signals representative of the counts of photons detected by the scintillators are processed by the data processor. The signal may be subjected to smoothing or stabilisation algorithms, averaged or otherwise operated on according to standard practices. A data processor may perform calculations based on the signal from the radiation detector or from a signal processor if present. The data processor may output information concerning the amount of radiation measured over a time interval, or it may further calculate derived properties of the scanned structure, usually in the form of a bulk density or a change in bulk density between radiation paths through the structure. The scanning method is carried out at a plurality of radially offset positions around the structure so that density data may be acquired at a variety of angles through the structure and a tomography algorithm may be used to provide information about the changes in density at different paths through the structure. In a preferred form the data from the detectors is operated on by the data processing unit using tomography algorithms in order to produce a graphical representation of the density or composition of the structure along different paths. The data processor may contain a calibration or information concerning the radiation source. The data processor output is may be connected a display or a (optionally wireless) transmission means so that a signal can be sent from the apparatus to a remote location. Alternatively a signal comprising data from the radiation detector itself may be sent, for processing at a remote location. A power supply is provided to power the photodetectors, data processor and control electronics and also to power motors for moving the apparatus. Movement of the scanning apparatus, for example to open and close the apparatus and to rotate the source and detector, may be accomplished by means of electrically or hydraulically powered motors or actuators The apparatus may be moved between different locations or orientations with respect to the structure where the method of the invention is repeated. In this way a record of the attenuation to radiation through each radiation path through the structure may be gathered and used to calculate the location of changes or to build a representation of the structure and its contents.

An example incorporating several optional features of the invention will be described with reference to the appended drawings.

Figure 1:
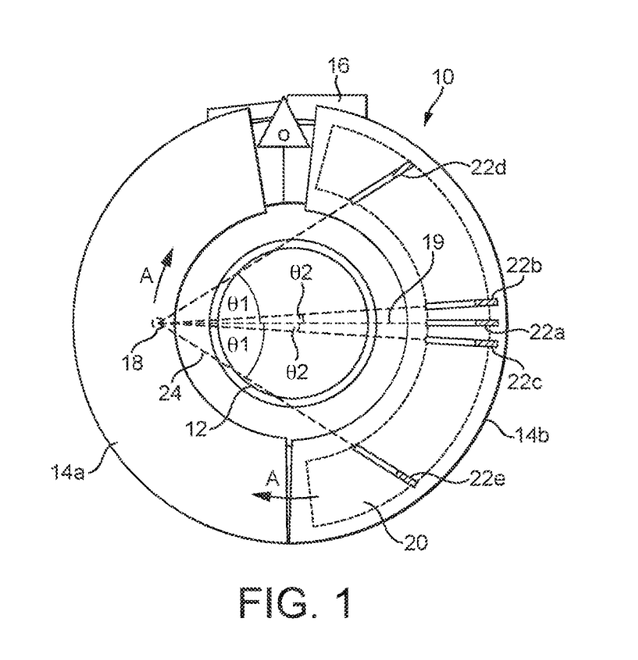
FIG. 1 is a schematic view of a section of a pipe enclosed within a scanning apparatus of the invention.
Figure 2:
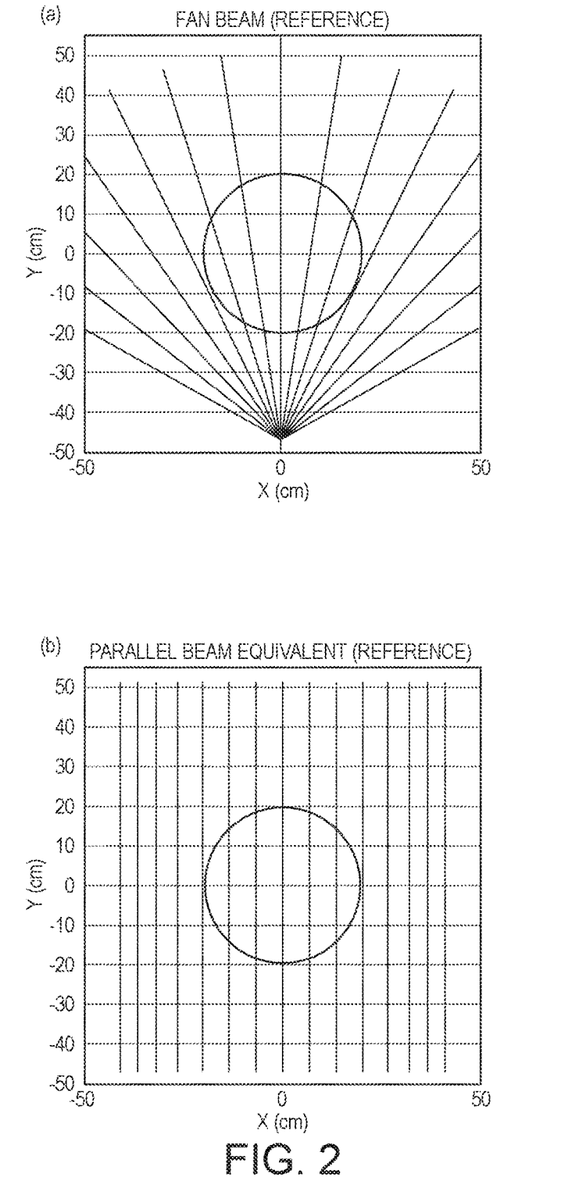
FIG. 2 is a schematic representation of the effect of a fan to parallel beam conversion.

FIG. 1 shows a pipe scanning apparatus 10 surrounding a pipeline 12 (shown in section). The scanning apparatus comprises a pair of hinged housings 14a & 14b which open and close by means of hydraulic apparatus 16. When the housings are open the apparatus may be moved around the pipe to be scanned and then closed around it. A source of gamma radiation 18 is located within housing 14a together with collimation and shielding to emit a collimated cone of radiation towards the detector array 20. An arcuate array 20 of 95 radiation detectors 22 (only five of which are shown, for illustration purposes) is located in housing 14b. The detectors comprise scintillation crystals, each coupled to a photodetector. The source and the detector array are fixed in relation to each other but are rotatable around the pipeline in the direction of arrows A. Each detector of the detector array detects radiation from the source which has passed along a portion of a cone-shaped path between the source and the detector. A number of radiation paths may be defined, each radiation path being between the source and each detector in the detector array. Each detector is directed towards the source and set within collimation and shielding materials to minimise its detection of scattered radiation.

In this example, detector 22a is located in the centre of the array, and the line of sight from the source to detector 22a follows the centre line between the detector array and the source. Detectors 22b and 22c form a conjugate pair, which are each offset from the centre line by angle θ2. Likewise, detectors 22d and 22e form a conjugate pair, which are each offset from the centre line by angle θ2. These five detectors are shown only for illustrative purposes. Detector array 20 consists, in this example, of 95 detectors, including 47 conjugate pairs.

When a radiation path intersects the pipe, as shown, for example, by the dashed line 24, the radiation is attenuated by the material of the pipe wall so that the radiation detected by a radiation detector in that path is less than the radiation detected by a detector located in a path which intersects less of the pipe material. In that way, information can be collected about the density of material along each radiation path and, by means of the rotation of the source and detector array and using a tomography algorithm, an image of the pipeline wall thickness may be assembled.

Figure 3:
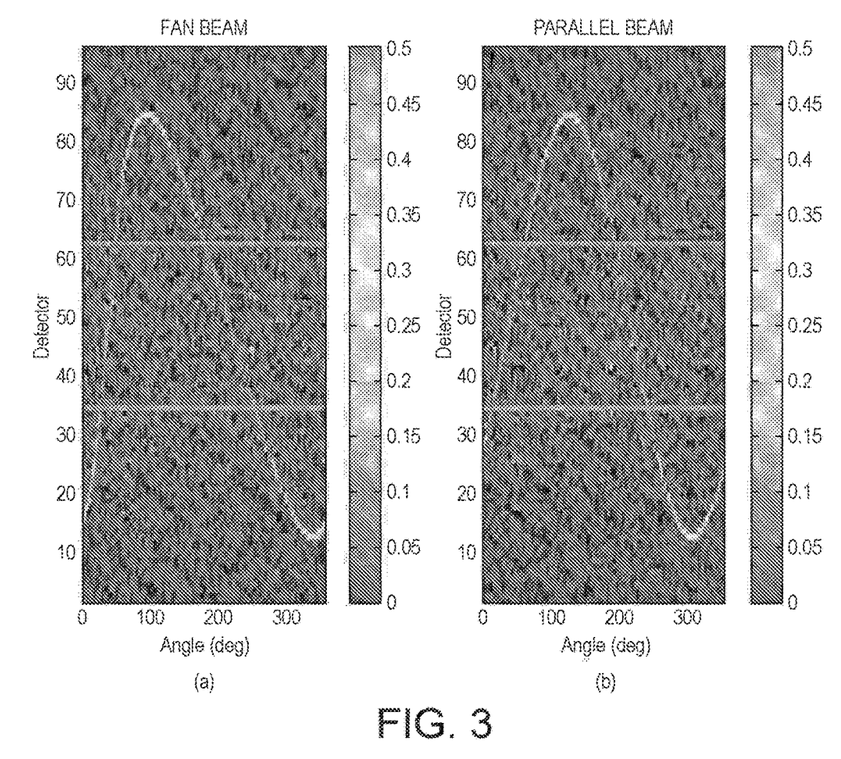
FIG. 3 shows the count rates for each of 95 detectors at different angles.

FIG. 3 shows a representation of a coloured matrix of individual detector number n (rows) and angle of source to the pipeline (columns). It will be appreciated that the coloured matrix represented as grey-scale in FIG. 1 may lose some detail from its original coloured form. T Count rates are number of counts per unit time, where unit time may be expressed in seconds or as the count period if all count periods are of equal duration.

In the method of the invention, with the source and detector array positioned at a start position, which is designated as 0° of angle, data is collected from each of the 95 detectors representing the number of counts of radiation received as the source and detector are rotated with respect to the pipe through 360°. In this example, data is collected at 1 degree increments of rotation. After a calibration adjustment to account for small differences between the detectors, a fan-to-parallel beam adjustment algorithm is applied to the data.

FIG. 3 clearly shows a sinusoidal pattern in the data. A single discontinuity in the density of the pipe material causes a sinusoidal variation in the data because each detector detects the same discontinuity at a different angular position. In this case a small steel bar was placed in the pipeline, for demonstration purposes. The fan to parallel conversion has rendered the asymmetric curve in FIG. 3(*a*) on the left, as a symmetrical sine wave in the parallel beam data in FIG. 3(*b*) on the right. In this parallel beam form each density variation produces sine waves, which are symmetric compared to the midplane (detector 48). This is important because any 2 detectors that are in symmetric positions compared to detector 48 (e.g. 47/49, 46/50, etc.), referred to as a conjugate pair, will see the same part of the object, but with a 180 degrees angular offset. From the symmetrical sine wave, it is clear that conjugate pairs of detectors read the same attenuation profile at an angular spacing of 180° from each other. Therefore in the case of missing data due to a malfunctioning detector it is possible to use data from the other one of the conjugate pair of which the malfunctioning detector forms a part.

The invention claimed is:

1. A scanning method which is a method of identifying a change in the density of an object, said change representing a difference between the density of said object at a first location and the density of said object at a second location adjacent said first location, the method comprising the steps of:
 a. arranging a source of ionizing radiation and a linear array of radiation detectors, where n is an integer from 1 to N, capable of detecting said radiation in such a way that
  i. radiation is emitted from the source in the direction of the array of radiation detectors,
  ii. radiation is emitted from the source towards any one of said radiation detectors along a radiation path, said radiation path being defined at each end by the source and the area of each detector facing said source;
  iii. up to N of said radiation paths may pass through said object; and
  iv. said source and said detector array are located in fixed positions relative to one another and movable along an arcuate scanning path around said object;
 wherein said detector array comprises a plurality of N radiation detectors D which are arranged symmetrically opposite said source in such a way that conjugate pairs of detectors are arranged at equal angles from the source;
 b. calibrating the detectors, wherein the calibration step includes obtaining an energy spectrum scan for each detector in the array;
 c. positioning the source and detector array at a known position on said scanning path;
 d. moving said source and detector array along said scanning path so that the source and detector array rotate through 360 degrees around said object;
 e. acquiring count data from each detector at a plurality of positions on said scanning path, said count data being related to the number of photons of radiation emitted by the source which have been detected by said detector during the count period;
 f. converting count data acquired by each detector at each position by means of a fan to parallel beam conversion algorithm to converted count data;
 g. selecting count data from at least one detector of each said conjugate pair;
 h. deriving information concerning the density of the object at different positions in the plane of the scanning path from said count data wherein information from the energy spectrum scan in step (b) is used to identify a broken or defective detector and, when the broken or defective detector has been identified, data from its conjugate pair is selected in step (g).

2. A method according to claim 1, wherein count data is selected from at least one detector of each said conjugate pair on the basis of the count data counted by each said detector.

3. A method according to claim 2, wherein the count data acquired by each detector of a conjugate pair is compared to determine whether either of said detectors is defective.

4. A method according to claim 2, wherein count data from a detector is compared with a predetermined range of value of counts which would be expected from the detector in order to determine if the detector is defective.

5. A method according to claim 1, wherein the count data acquired by each detector of a conjugate pair is compared to determine whether either of said detectors is defective.

6. A method according to claim 1, wherein count data from a detector is compared with a predetermined range of value of counts which would be expected from the detector in order to determine if the detector is defective.

7. A method according to claim 1, wherein said calibration is carried out in the absence of the object to be scanned.

8. A method according to claim 7, wherein information from the energy spectrum scan is used to identify suitable energy windows within which to count photons detected by the detector.

9. A method according to claim 1, wherein the calibration step is carried out in the same or substantially the same environmental conditions as will be used for the scan.

10. A method according to claim 9, wherein information from the energy spectrum scan is used to identify suitable energy windows within which to count photons detected by the detector.

11. A method according to claim 1, wherein information from the energy spectrum scan is used to identify suitable energy windows within which to count photons detected by the detector.

12. A method according to claim 1, wherein information from the calibration is used to identify which detector of a conjugate pair of detectors offers the higher resolution of the pair.

13. A method according to claim 12, wherein count data from the detector within a conjugate pair which offers the higher resolution is selected in step (g).

14. A scanning apparatus according to the invention comprises: a source of ionizing radiation and an array of radiation detectors, capable of detecting said radiation, said source and detector array being arranged in such a way that
  i. radiation is emitted from the source in the direction of the array of radiation detectors,
  ii. radiation is emitted from the source towards any one of said radiation detectors along a radiation path, said radiation path being defined at each end by the source and the area of each detector facing said source;
  iii. up to N of said radiation paths may pass through an object which is to be scanned; and
  iv. said source and said detector array are located in fixed positions relative to one another and movable along an arcuate scanning path around said object;
wherein said detector array comprises a plurality of N radiation detectors D which are symmetrically arranged opposite said source in such a way that conjugate pairs of detectors are arranged at equal angles from the source;
means to move said source and detector array along said scanning path so that the source and detector array rotate through 360 degrees around said object;
data processing means which is programmed to
  a. acquire count data from each detector, at a plurality of positions on said scanning path, said count data being related to the number of photons of radiation emitted by the source which have been detected by said detector during the count period;
  b. convert count data acquired by each detector at each position by means of a fan to parallel beam conversion algorithm to converted count data;
  c. select count data from at least one detector of each said conjugate pair wherein the data processing means is programmed to use information from an energy spectrum scan from a calibration to identify a broken or defective detector and, when the broken or defective detector has been identified, select data from its paired conjugate detector; and
  d. derive information concerning the density of the object at different positions in the plane of the scanning path from said count data.

\* \* \* \* \*